(12) United States Patent
Dunham

(10) Patent No.: US 7,835,011 B2
(45) Date of Patent: Nov. 16, 2010

(54) SYSTEMS AND METHODS FOR DETERMINING A POSITION OF A SUPPORT

(75) Inventor: Bruce Matthew Dunham, Mequon, WI (US)

(73) Assignee: General Electric Company, Schenectady, NY (US)

( * ) Notice: Subject to any disclaimer, the term of this patent is extended or adjusted under 35 U.S.C. 154(b) by 367 days.

(21) Appl. No.: 11/336,035

(22) Filed: Jan. 20, 2006

(65) Prior Publication Data

US 2007/0171428 A1 Jul. 26, 2007

(51) Int. Cl.
*G01B 11/02* (2006.01)
(52) U.S. Cl. .................................... 356/500; 378/195
(58) Field of Classification Search ............... 356/500; 378/20, 195
See application file for complete search history.

(56) References Cited

U.S. PATENT DOCUMENTS

| | | | | |
|---|---|---|---|---|
| 2,418,786 A * | 4/1947 | Nadig et al. | ................. | 356/498 |
| 3,572,935 A * | 3/1971 | Howell et al. | ................. | 356/498 |
| 3,884,580 A | 5/1975 | Webster et al. | | |
| 4,052,603 A | 10/1977 | Karlson | | |
| 4,261,107 A * | 4/1981 | Coleman et al. | ............ | 250/550 |
| 4,457,625 A * | 7/1984 | Greenleaf et al. | ........... | 356/511 |
| 4,621,926 A * | 11/1986 | Merry et al. | ................. | 356/508 |
| 4,701,053 A | 10/1987 | Ikenaga | | |
| 5,127,735 A * | 7/1992 | Pitt | ............................ | 356/500 |
| 5,260,761 A * | 11/1993 | Barker | ......................... | 356/4.1 |
| 6,028,910 A * | 2/2000 | Kirchner et al. | ............... | 378/22 |
| 6,069,700 A * | 5/2000 | Rudnick et al. | ............. | 356/511 |
| 6,196,715 B1* | 3/2001 | Nambu et al. | ............... | 378/197 |
| 6,324,249 B1* | 11/2001 | Fazzio | .......................... | 378/22 |
| 6,690,474 B1* | 2/2004 | Shirley | ....................... | 356/603 |
| 7,079,258 B2* | 7/2006 | Selbach et al. | .............. | 356/502 |
| 7,130,058 B2* | 10/2006 | Kim et al. | .................... | 356/511 |
| 7,199,382 B2* | 4/2007 | Rigney et al. | ............. | 250/492.1 |
| 7,403,290 B1* | 7/2008 | Freimann | .................... | 356/512 |
| 7,433,507 B2* | 10/2008 | Jabri et al. | .................. | 382/132 |
| 2002/0188194 A1* | 12/2002 | Cosman | ...................... | 600/426 |
| 2003/0030779 A1* | 2/2003 | Hara | ............................ | 355/53 |
| 2003/0185339 A1* | 10/2003 | Heumann et al. | ............. | 378/19 |
| 2004/0223163 A1* | 11/2004 | Kakuchi | ..................... | 356/515 |
| 2005/0157841 A1* | 7/2005 | Chopra | .......................... | 378/22 |

OTHER PUBLICATIONS

Optics, Fourth Edition by Eugene Hect, published by Addison Wesley 2002.*

* cited by examiner

*Primary Examiner*—Tarifur Chowdhury
*Assistant Examiner*—Jonathon D Cook
(74) *Attorney, Agent, or Firm*—Armstrong Teasdale LLP

(57) ABSTRACT

A method for determining a change in a position of a support is described. The method includes determining the change in the position of the support used in an imaging system, where determining the change includes computing the position by operating a photodetector configured to detect laser energy that provides information regarding the position.

20 Claims, 5 Drawing Sheets

SYSTEMS AND METHODS FOR DETERMINING A POSITION OF A SUPPORT

BACKGROUND OF THE INVENTION

This invention relates generally to imaging systems and more particularly to, systems and methods for determining a position of a support used within an imaging system.

In at least one known computed tomography (CT) imaging system configuration, an x-ray source projects a fan-shaped beam which is collimated to lie within an x-y plane of a Cartesian coordinate system and generally referred to as the "imaging plane". The x-ray beam passes through a subject, such as a patient, being imaged. The beam, after being attenuated by the subject, impinges upon an array of radiation detectors. The intensity of the attenuated beam radiation received at the detector array is dependent upon the attenuation of the x-ray beam by the subject. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the subject to be imaged so that the angle at which the x-ray beam intersects the subject constantly changes. A group of x-ray attenuation measurements, i.e., projection data, from the detector array at one gantry angle is referred to as a "view". A "scan" of the subject includes a set of views made at different gantry angles or view angles, during one revolution of the x-ray source and detector.

In an axial scan, the projection data is processed to construct an image that corresponds to a two dimensional slice taken through the subject. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

As CT scanners continue to use smaller detector element or cell sizes, a plurality of constraints applied to table positioning accuracy and stability become more stringent. In addition, reconstruction techniques using variable table speed during the CT scan make an accurate measurement of table position more critical.

BRIEF DESCRIPTION OF THE INVENTION

A method for determining a change in a position of a support is described. The method includes determining the change in the position of the support used in an imaging system, where determining the change includes computing the position by operating a photodetector configured to detect laser energy that provides information regarding the position.

A system for determining a change in a position is described. The system includes an imaging system comprising a support, a photodetector configured to detect laser energy that provides information regarding the position of the support, and a processor configured to compute the change in the position of the support.

A system for determining a change in a position of a support is provided. The system includes an x-ray source configured to generate x-rays that pass through a subject, an x-ray detector configured to detect the x-rays after the x-rays pass through the subject, a support configured to support the subject, a photodetector configured to detect laser energy that provides information regarding the position, and a processor configured to compute the change in the position of the support.

DETAILED DESCRIPTION OF THE INVENTION

Figure 1:
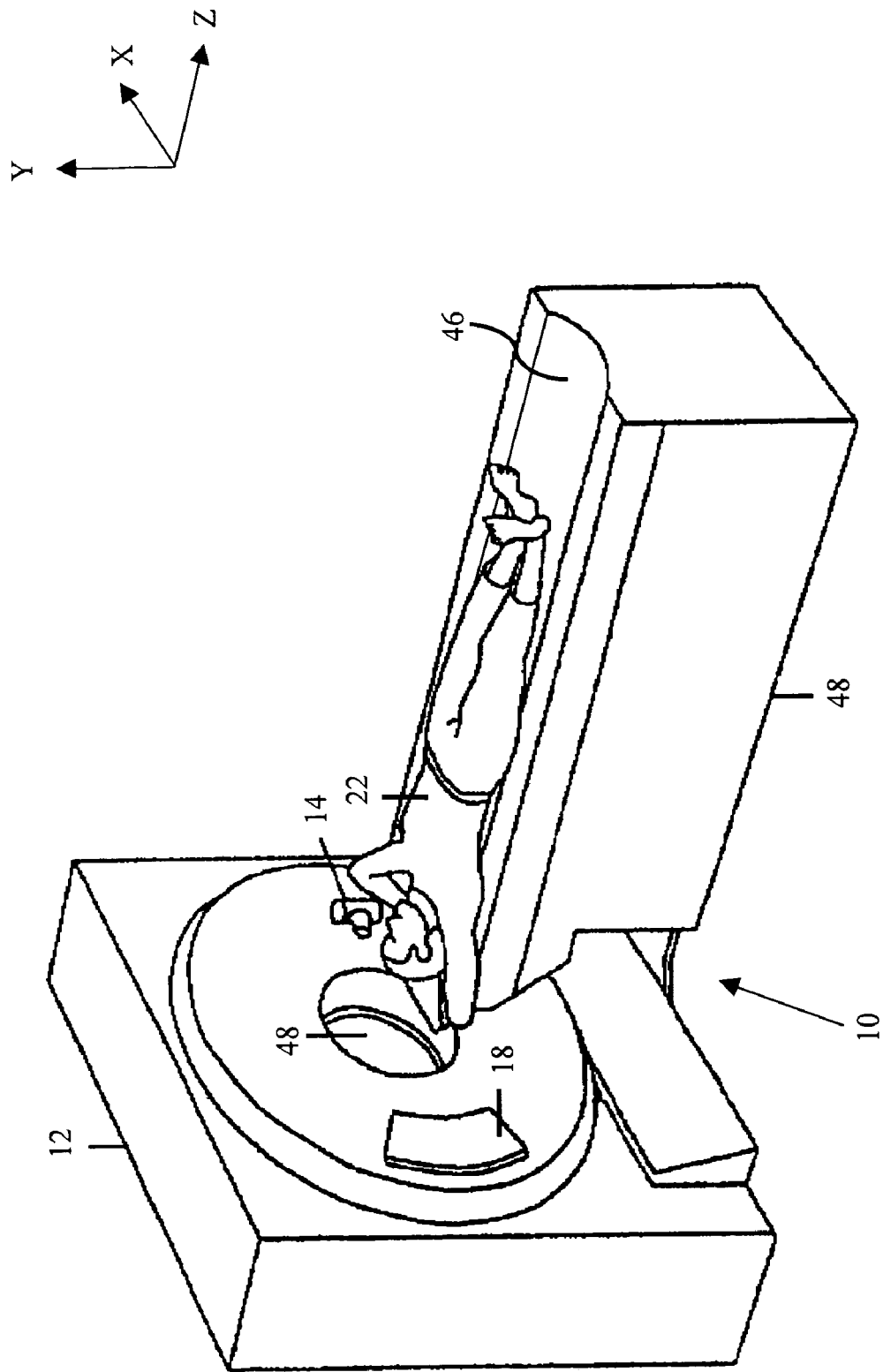
FIG. 1 is an isometric view of an embodiment of a computed tomography (CT) system.
Figure 2:
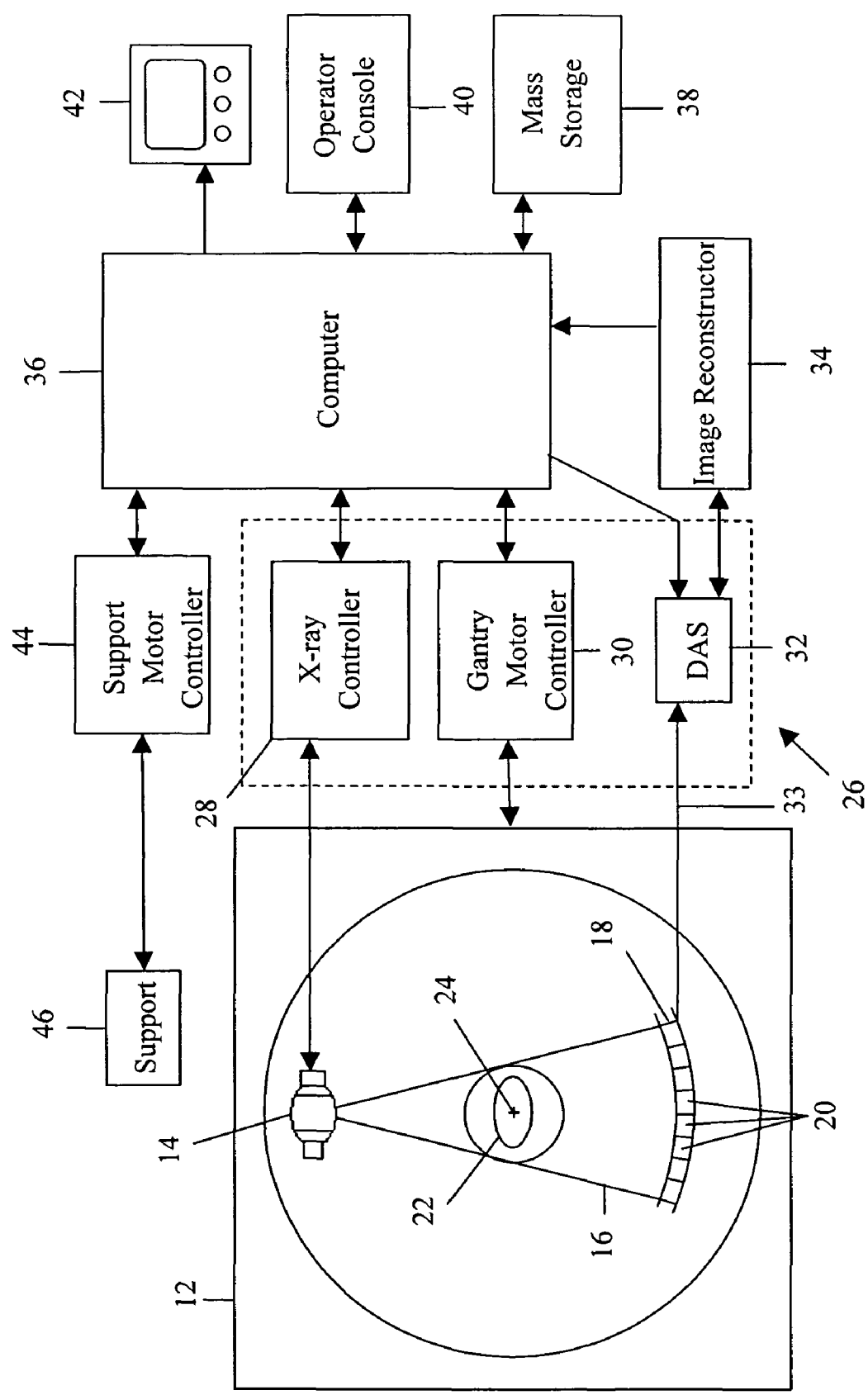
FIG. 2 is a block diagram of an embodiment of the CT system of FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12.

The beam of x-rays generated by x-ray source 14 is collimated by a collimator. The collimated x-ray beams generated by x-ray source 14 are shaped like a fan. The collimated x-ray beams then pass through a subject 22, such as a medical patient or a phantom, located along a z-axis. In an alternative embodiment, an object, such as a bag or a box, may be scanned by CT imaging system 10.

Detector array 18 includes a plurality of detector elements 20 which together sense the projected x-rays that pass through subject 22. Each detector element 20 produces an analog electrical signal or an analog trigger signal that represents an intensity of an impinging x-ray beam and hence the attenuation of the beam as it passes through subject 22. During a scan to acquire x-ray projection data, gantry 12 and a plurality of components mounted thereon rotate about a center of rotation 24. Detector array 18 may be fabricated in a single slice or multi-slice configuration. In a multi-slice configuration, detector array 18 has a plurality of rows of detector elements 20, one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples a plurality of analog trigger signals 33 or projection data from detector elements 20 and converts the analog trigger signals 33 to a plurality of digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a support motor controller 44 which controls a motorized support 46, such as a couch or a pad. Support 46 supports subject 22 to position subject 22 in gantry 12. Particularly, support 46 moves portions of subject 22 through a gantry opening 48. Support 46 is located on top of a table or base 48, and support 46 moves with respect to table 48. Support motor controller 44 controls movement of support 48 in at least one of an x-direction, a y-direction, and a z-direction. The x-direction is parallel to an x-axis, the y-direction is parallel to a y-axis, and the z-direction is parallel to the z-axis.

Although the specific embodiment mentioned above refers to a third generation CT system 10, a fourth generation CT system that has a stationary detector and a rotating x-ray source or a fifth generation CT system that has a stationary detector and a stationary x-ray source may be used instead of the third generation CT imaging system 10. In another alternative embodiment, an x-ray system including an x-ray source and an x-ray detector may be used instead of the CT imaging system 10. In an alternative embodiment, systems and methods for determining a position of a support apply to other imaging systems, such as, a positron emission tomography (PET) imaging system, a magnetic resonance imaging (MRI) system, a CT-PET system, an ultrasound imaging system, and any other imaging system that includes support 46.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

Figure 3:
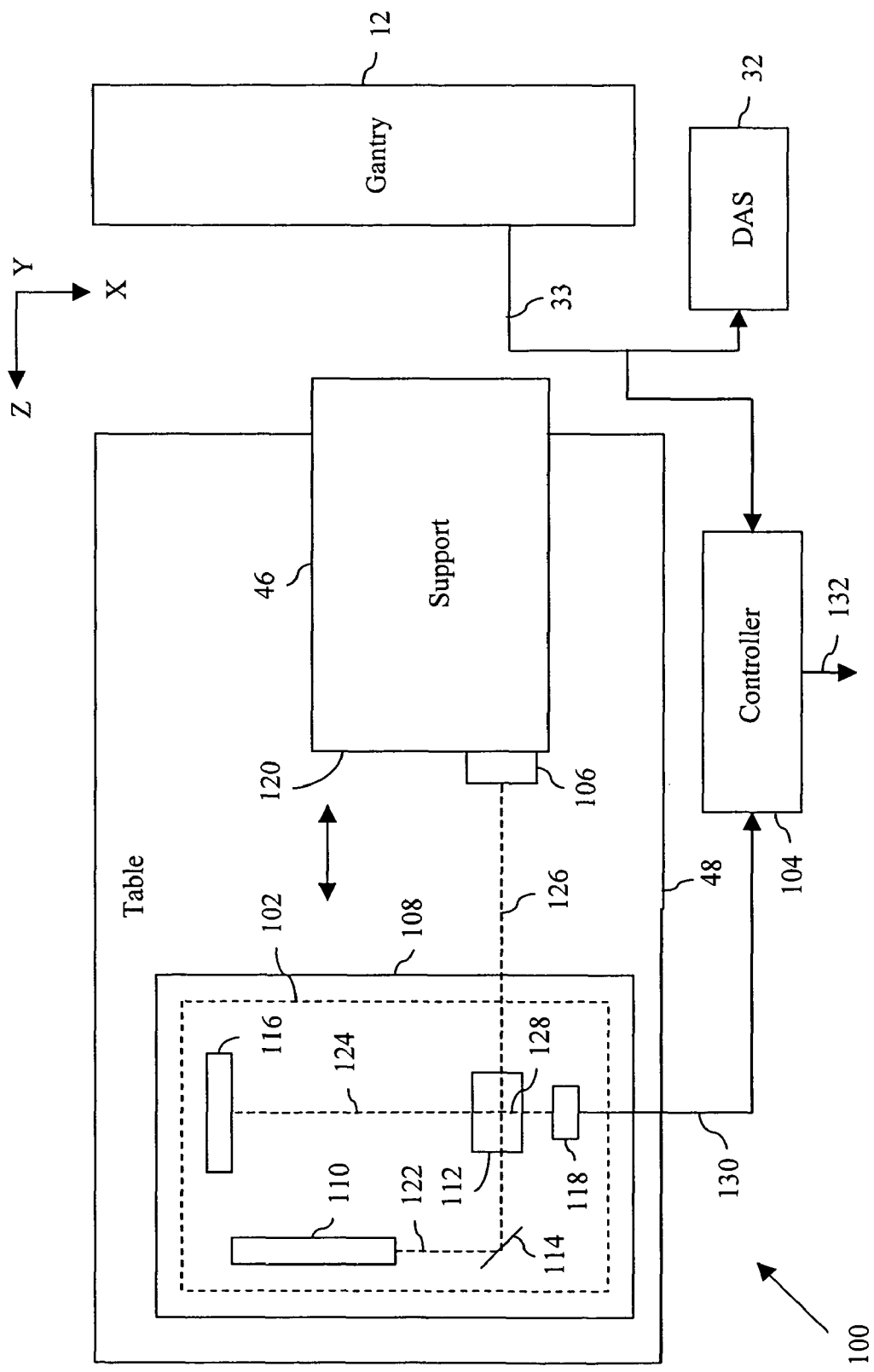
FIG. 3 is a top view of an embodiment of a system for determining a position of a support.

FIG. 3 is a block diagram of an embodiment of a system 100 for determining a position of a support. System 100 includes an interferometer 102, a controller 104, a reflective surface 106, and support 46. Interferometer 102 is attached, such as glued and/or bolted, to a support plate 108. In an alternative embodiment, system 100 may not include support plate 108 and interferometer 102 is attached, such as glued and/or bolted, to table 48. Support plate 108 is attached, such as glued and/or bolted, to table 48. As used here, the term 'controller' is not limited to just those integrated circuits referred to in the art as a controller, but broadly refers to a computer, a processor, a microcontroller, a microcomputer, a programmable logic controller, an application specific integrated circuit, and any other programmable circuit, and these terms are used interchangeably herein. Alternatively, controller 104 can be any of support motor controller 44, x-ray controller 28, gantry motor controller 30, and computer 36. Interferometer 102 includes a laser source 110, a beam splitter 112, a plurality of reflective surfaces 114 and 116, and a photodetector 118, such as a laser beam detector. Examples of any of reflective surfaces 106, 114, and 116 include a prism and a mirror. Reflective surface 106 is attached, such as bolted and/or glued, to a side surface 120 of support 46 so that reflective surface 106 faces interferometer 102 and is in a line-of-sight of beam splitter 112. In an alternative embodiment, side surface 120 of support 46 is reflective and system 100 excludes reflective surface 106. In another alternative embodiment, reflective surface 106 is attached to subject 22 to determine a position of subject 22. In another alternative embodiment, reflective surface 106 is attached to the object to determine a position of the object.

Laser source 110 generates a laser beam 122 that is directed towards reflective surface 114. An example of interferometer 102 includes a Michelson interferometer that measures a position of support 46 with a variance ranging from 0.1 micron to less than 1 micron, which is a wavelength of laser beam 122. In an alternative embodiment, interferometer 102 does not include reflective surface 114 and laser source 110 is placed so that laser beam 122 is incident directly on beam splitter 112. Laser beam 122 is directed by reflective surface 114 towards beam splitter 112. Beam splitter 112 splits laser beam 122 into a plurality of laser beams 124 and 126. Beam splitter 112 directs laser beam 126 towards reflective surface 106 and laser beam 124 towards reflective surface 116. Reflective surface 106 reflects laser beam 126 to generate a laser beam (not shown) that is directed towards beam splitter 112. Reflective surface 116 reflects laser beam 124 to generate a laser beam (not shown) that is directed towards beam splitter 112. Beam splitter 112 receives the laser beams reflected from reflective surfaces 106 and 116 and splits the laser beams to generate a laser beam 128 that includes an interference fringe pattern. Beam splitter 112 directs laser beam 128 towards photodetector 118. Photodetector 118 detects the interference fringe pattern within laser beam to generate a plurality of electric pulses 130. For example, photodetector 118 generates a single electric pulse upon detecting one fringe within the interference fringe pattern. The interference fringe pattern is generated upon movement of support 46 along the z-axis. In an alternative embodiment, instead of interferometer 102, a commercially available device, such as a laser distance sensor available from Keyence™ Corporation, is used to generate electric pulses 130. Another example of the commercial available device includes a system that measures a position of support 46 with a variance ranging from and including 0.01 millimeters (mm) to 0.1 mm, and that determines a position of support 46 at a frequency ranging up to 50 kilohertz (kHz).

Controller 104 receives electric pulses 130 from photodetector 118, converts electric pulses 130 from an analog to a digital form, counts a number of electric pulses 130, and determines a z-position of support 46 based on the count. Controller 104 includes an analog-to-digital converter that converts electric pulses 130 from an analog to a digital form. Alternatively, the analog-to-digital converter is located outside controller 104. Controller 104 counts a number of electric pulses 130 upon converting electric pulses 130 into a digital form. Controller 104 calculates a first z-position 132 by generating a result and dividing the result by two. Controller 104 calculates the result by multiplying a wavelength of laser beam 122 with a number of electric pulses 33 counted during movement of support 46 from an initial z-position to first z-position 132. A z-position is along the z-axis.

Controller 104 outputs the first z-position 132 upon receiving analog trigger signals 33 from detector array 18. For example, controller 104 outputs the first z-position 132 upon receiving trigger signals 33 from detector array 18 acquired at a particular view or gantry angle, such as, for example, zero degrees or one degree, of gantry 12. Controller 104 outputs a plurality of z-positions including the first z-position 132. As an example, controller 104 outputs the plurality of z-positions at a frequency ranging from and including 100 Hertz (Hz) to 10 kHz, where the frequency is a frequency of acquisition by CT imaging system 10 of a plurality of views of gantry 12. As another example, controller 104 outputs the first z-position 132 upon receiving trigger signals 33 acquired at a view angle of zero degrees and outputs a second z-position upon receiving analog trigger signals 33 acquired at a view angle of twenty degrees. In the example, controller 104 determines the second z-position by counting a number of electrical pulses 33 received during a time of movement of support 46 from the first z-position to the second z-position, multiplying a wavelength of laser beam 122 with the number of the electric pulses 33 counted to generate an outcome, and dividing the outcome by two.

In an alternative embodiment, controller 104 outputs the plurality of z-positions at a frequency faster than a frequency of acquisition of a plurality of views to provide feedback to support motor controller 44 or to measure a vibration of support 46. For example, controller 104 does not wait to receiving analog trigger signals 33 acquired at a particular view angle before outputting the first z-position 132. Controller 104 transmits the plurality of z-positions to mass storage device 38.

Image reconstructor 34 retrieves at least one of the z-positions from mass storage device 38 to reconstruct a plurality of images at a plurality of views. For example, image reconstructor 34 reconstructs a first image acquired at a first view angle and at the first z-position 132, appends the first z-position 132 to the first image, reconstructs a second image acquired at a second view angle and at the second z-position, and appends the second z-position to the second image. Computer 32 retrieves a z-position from mass storage device 38 and the z-position is used by the operator to diagnose an image reconstructed at the z-position.

Figure 4:
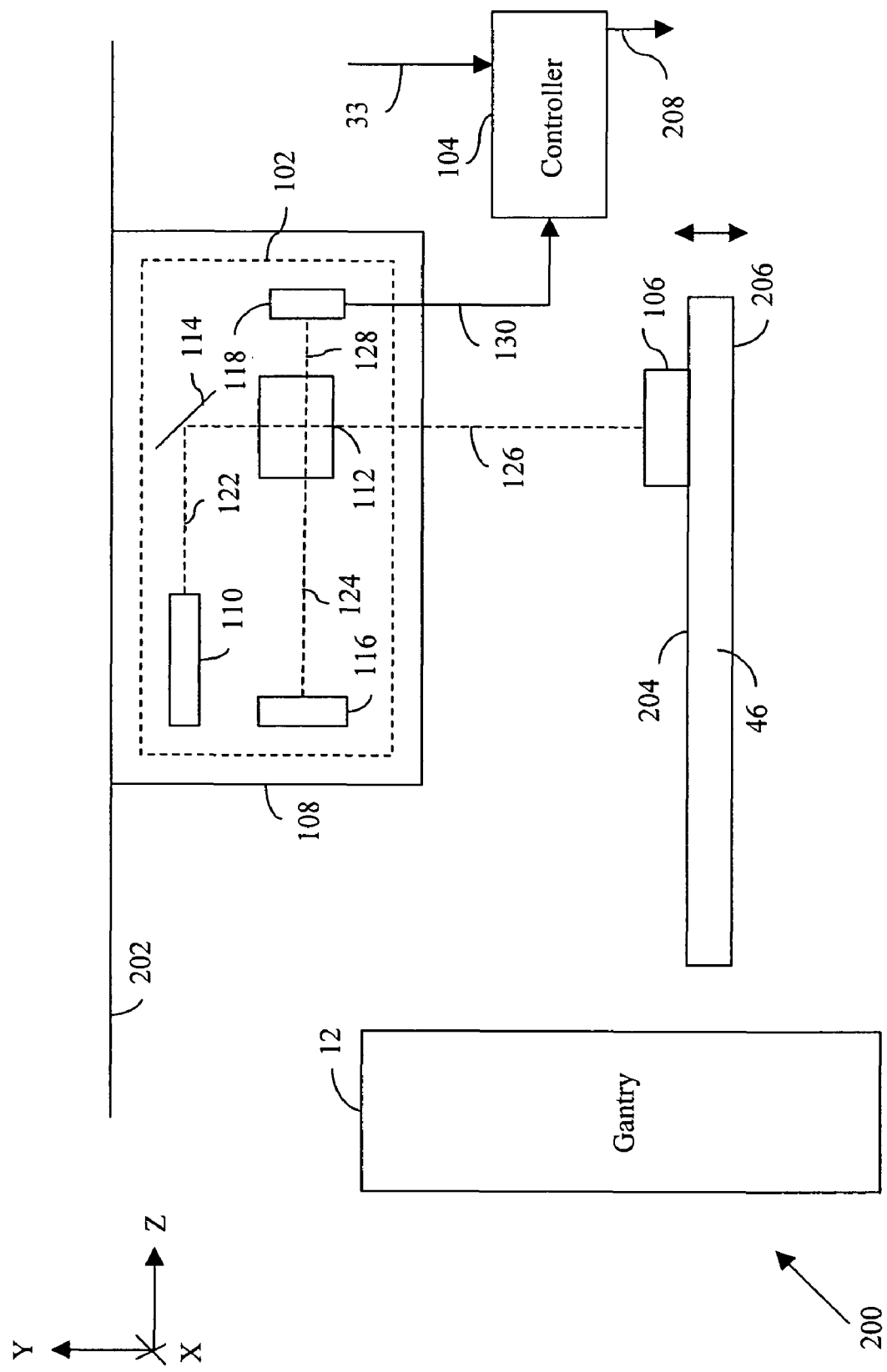
FIG. 4 is a side view of an embodiment of a system for determining a position of a support.

FIG. 4 is a block diagram of an alternative embodiment of a system 200 for determining a position of a support. System 200 includes interferometer 102, controller 104, reflective surface 106, and support 46. Support plate 108 is attached, such as glued and/or bolted, to a ceiling 202 of a scanning room in which CT imaging system 10 is placed. In an alternative embodiment, system 200 may not include support plate 108 and interferometer 102 is attached, such as glued and/or bolted, to the ceiling 202. In an alternative embodiment, interferometer 102 is attached to an item that suspends interferometer 102 above a height of support 46 in the z-direction. Reflective surface 106 is attached, such as bolted and/or glued, to a top surface 204 of support 46 so that reflective surface 106 faces interferometer 102 and is in a line-of-sight of beam splitter 112. In another alternative embodiment, interferometer 102 is attached directly or via support plate 108 to a floor of the scanning room and reflective surface 106 is attached to a bottom surface 206 of support 46. In another alternative embodiment, interferometer 102 is attached to the floor of the scanning room, system excludes reflective surface 106, and bottom surface 206 is reflective. In an alternative embodiment, top surface 204 of support 46 is reflective and system excludes reflective surface 106.

The interference fringe pattern is generated in a similar manner described above upon movement of support 46 along the y-axis. Controller 104 receives electric pulses 130 from photodetector 118, converts electric pulses 130 from an analog to a digital form, counts a number of electric pulses 130, and determines a y-position of support 46 based on the count. Controller 104 calculates a first y-position 208 by generating an amount and dividing the amount by two. Controller 104 calculates the amount by multiplying a wavelength of laser beam 122 with a number of electric pulses 33 counted during movement of support 46 from an initial y-position to first y-position 208. A y-position is along the y-axis.

Controller 104 outputs the first y-position 208 upon receiving analog trigger signals 33 from detector array 18. For example, controller 104 outputs the first y-position 208 upon receiving trigger signals 33 from detector array 18 acquired at a particular view or gantry angle, such as, for example, one degree or two degrees, of gantry 12. Controller 104 outputs a plurality of y-positions including the first y-position 208. As an example, controller 104 outputs the plurality of y-positions at a frequency ranging from and including 100 Hz to 10 kHz, where the frequency is a frequency of acquisition by CT imaging system 10 of a plurality of views of gantry 12. As another example, controller 104 outputs the first y-position 208 upon receiving analog trigger signals 33 acquired at a view angle of ten degrees and outputs a second y-position upon receiving analog trigger signals 33 acquired at a view angle of twenty degrees. In the example, controller 104 determines the second y-position by counting a number of electrical pulses 33 received during a time of movement of support 46 from the first y-position 208 to the second y-position, multiplying a wavelength of laser beam 122 with the number of the electric pulses 33 counted to generate a product, and dividing the product by two.

In an alternative embodiment, controller 104 outputs the plurality of y-positions at a frequency faster than a frequency of acquisition of a plurality of views to provide feedback to support motor controller 44 or to measure a vibration of support 46. For example, controller 104 does not wait to receive analog trigger signals 33 acquired at a particular view angle before outputting the first y-position 208. Controller 104 transmits the plurality of y-positions to mass storage device 38.

Image reconstructor 34 retrieves at least one of the y-positions from mass storage device 38 to reconstruct a plurality of images at a plurality of views. For example, image reconstructor 34 reconstructs the first image acquired at the first view angle and at the first y-position 208, appends the first y-position 208 to the first image, reconstructs the second image acquired at a second view angle and at the second y-position, and appends the second y-position to the second image. Computer 32 retrieves a y-position from mass storage device 38 and the y-position is used by the operator to diagnose an image reconstructed at the y-position.

Figure 5:
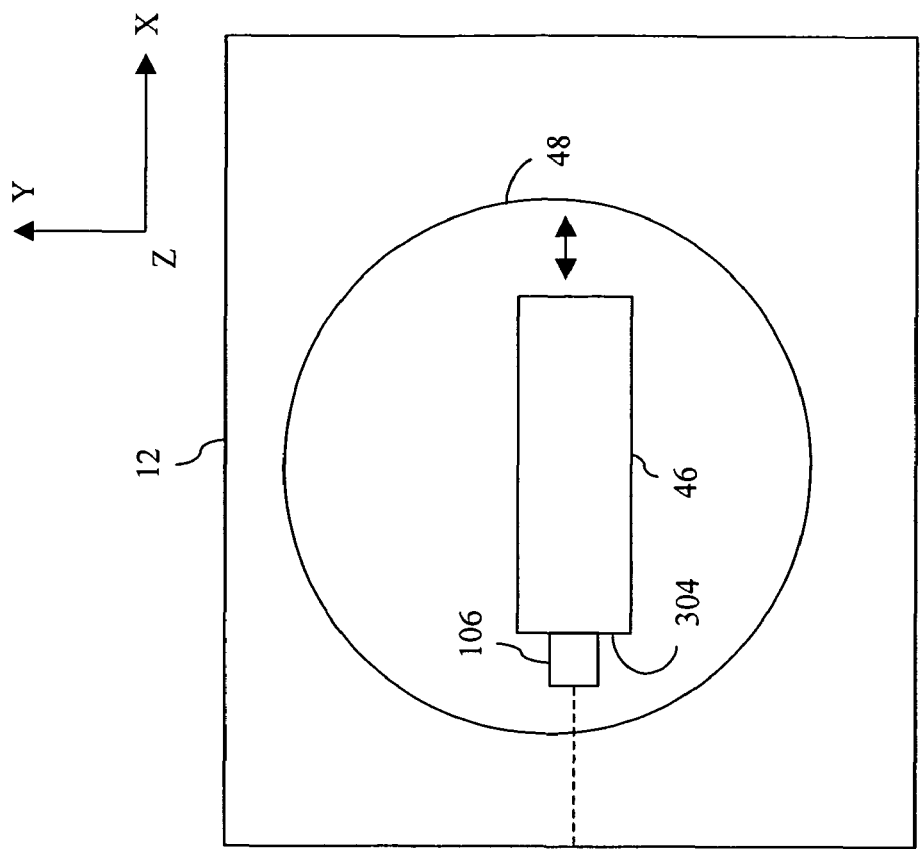
FIG. 5 is a front view of an embodiment of a system for determining a position of a support.
Figure 5:
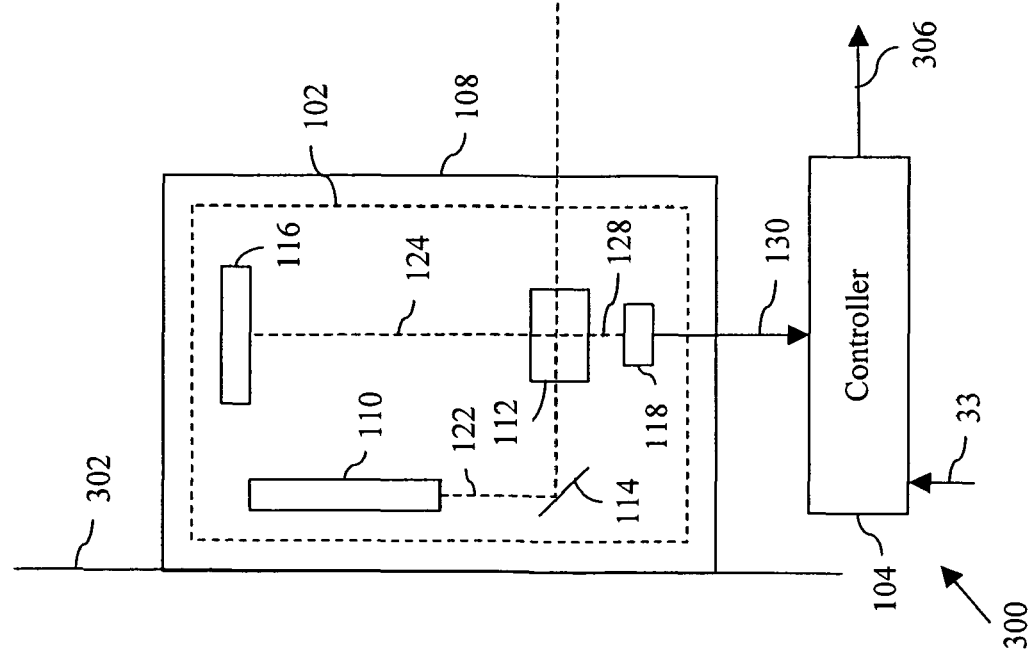

FIG. 5 is a block diagram of an alternative embodiment of a system 300 for determining a position of a support. System 300 includes interferometer 102, controller 104, reflective surface 106, and support 46. Support plate 108 is attached, such as glued and/or bolted, to a side wall 302 of the scanning room. In an alternative embodiment, system 300 may not include support plate 108 and interferometer 102 is attached, such as glued and/or bolted, to side wall 302. In another alternative embodiment, interferometer 102 attached to an item that suspends interferometer 102 to face reflective surface 106. Reflective surface 106 is attached, such as bolted and/or glued, to a side surface 304 of support 46 so that reflective surface 106 faces interferometer 102. In an alternative embodiment, side surface 304 of support 46 is reflective and system excludes reflective surface 106.

The interference fringe pattern is generated in a similar manner described above upon movement of support 46 along the x-axis. Controller 104 receives electric pulses 130 from photodetector 118, converts electric pulses 130 from an analog to a digital form, counts a number of electric pulses 130, and determines an x-position of support 46 based on the count. Controller 104 calculates a first x-position 306 by generating a solution and dividing the solution by two. Controller 104 calculates the solution by multiplying a wavelength of laser beam 122 with a number of electric pulses 33 counted during movement of support 46 from an initial x-position to first x-position 306. An x-position is along the x-axis.

Controller 104 outputs the first x-position 306 upon receiving analog trigger signals 33 from detector array 18. For example, controller 104 outputs the first x-position 306 upon receiving trigger signals 33 from detector array 18 acquired at a particular view or gantry angle, such as, for example, one degree or two degrees, of gantry 12. Controller 104 outputs a plurality of x-positions including the first x-position 306. As an example, controller 104 outputs the plurality of x-positions at a frequency ranging from and including 100 Hz to 10 kHz, where the frequency is a frequency of acquisition by CT imaging system 10 of a plurality of views of gantry 12. As another example, controller 104 outputs the first x-position 306 upon receiving analog trigger signals 33 acquired at a view angle of ten degrees and outputs a second x-position upon receiving analog trigger signals 33 acquired at a view angle of twenty degrees. In the example, controller 104 determines the second x-position by counting a number of electrical pulses 33 received during a time of movement of support 46 from the first x-position 306 to the second x-position, multiplying a wavelength of laser beam 122 with the number of the electric pulses 33 counted to generate an output, and dividing the output by two.

In an alternative embodiment, controller 104 outputs the plurality of x-positions at a frequency faster than a frequency of acquisition of a plurality of views to provide feedback to support motor controller 44 or to measure a vibration of support 46. For example, controller 104 does not wait to receiving analog trigger signals 33 acquired at a particular view angle before outputting the first x-position 306. Controller 104 transmits the plurality of x-positions to mass storage device 38.

Image reconstructor 34 retrieves at least one of the x-positions from mass storage device 38 to reconstruct a plurality of images at a plurality of views. For example, image reconstructor 34 reconstructs the first image acquired at the first view angle and at the first x-position 306, appends the first x-position 306 to the first image, reconstructs the second image acquired at a second view angle and at the second x-position, and appends the second x-position to the second image. Computer 32 retrieves an x-position from mass storage device 38 and the x-position is used by the operator to diagnose an image reconstructed at the x-position.

In an alternative embodiment, controller 104 outputs a combination of at least one of the x-positions, at least one of the y-positions, and at least one of the z-positions at a frequency ranging from and including 100 Hz to 10 kHz, where the frequency is a frequency of acquisition by CT imaging system 10 of a plurality of views of gantry 12. As an example, controller 104 outputs the first x-position 306 upon receiving analog trigger signals 33 acquired at a view angle of two degrees and outputs the first y-position 208 upon receiving trigger signals 33 acquired at a view angle of twenty degrees. As another example, controller 104 outputs the first y-position 208 upon receiving trigger signals 33 acquired at a view angle of ten degrees and outputs the first x-position 132 upon receiving analog trigger signals 33 acquired at a view angle of thirty degrees.

It is noted that in another alternative embodiment, a plurality of inteferometers, such as interferometer 102, or commercial laser distance sensors can be placed in any combination of the x, y, and z directions, to determine a position of support 46 along a combination of the x, y, and z axes. For example, interferometer 102 is placed on support 108 to obtain at least one of the z-positions and another interferometer 102 is attached to ceiling 202 to obtain at least one of the y-positions. It is noted that in all the embodiments described above, reflective surface 106 faces interferometer 102 and is in a line-of-sight of beam splitter 112.

Technical effects of the herein described systems and methods for determining a position of a support include accurately determining, in real time, a position or a vibration of support used in an imaging system. A position or vibration of support 46 moving at a variable speed in at least one of the x, y, and directions is accurately determined by using interferometer 102. Other technical effects include associating an image with a corresponding position during an image reconstruction process. Further technical effects include correcting, by image reconstructor 34, for artifacts in an image induced by position errors or vibrations by considering a position of support 46 during a reconstruction of the image.

While the invention has been described in terms of various specific embodiments, those skilled in the art will recognize that the invention can be practiced with modification within the spirit and scope of the claims.

What is claimed is:

1. A method for generating an X-ray image of a subject positioned on a first support within an X-ray imaging system, said method comprising:

acquiring X-ray image data of the subject at a view angle with the first support at each position of a plurality of positions, each of said positions including an X-position, a Y-position, and a Z-position;

generating a beam of light;

reflecting a first portion of the beam of light from the first support to generate a reflected beam;

combining the reflected beam with a second portion of the beam of light to generate a combined beam, the combined beam including an interference fringe pattern;

counting a number of fringes within the interference fringe pattern of the combined beam of light;

generating a pulsed electric signal representative of the counted number of fringes;

determining a change in the X-position, the Y-position, and the Z-position of the first support by computing the X-position, the Y-position, and the Z-position using the pulsed electric signal to generate a measurement of the position of the first support for each of the plurality of positions; and reconstructing the X-ray image of the subject using the acquired X-ray image data and the generated measurement of the first support at each of the plurality of positions.

2. A method in accordance with claim 1 wherein generating a beam of light and reflecting the beam of light further comprise:

generating a first laser beam;

generating a second laser beam and a third laser beam by splitting the first laser beam; and generating a fourth laser beam by directing the second laser beam towards a reflective surface on the first support to generate the reflected beam.

3. A method in accordance with claim 2 wherein generating a beam of light and reflecting the beam of light further comprises generating a fifth laser beam by directing the third laser beam towards a second reflective surface coupled to a second support.

4. A method in accordance with claim 3 further comprising:

generating the interference fringe pattern of the combined beam by combining the fourth and the fifth laser beams; and generating the pulsed electrical signal by detecting the interference fringe pattern.

5. A method in accordance with claim 1 further comprising outputting the at least one position to an image reconstructor.

6. A method in accordance with claim 1 further comprising outputting the at least one position upon receiving the image data from a detector array of the imaging system.

7. A method in accordance with claim 1 further comprising outputting the at least one position upon receiving the X-ray image data at the view angle from a detector array of the X-ray imaging system.

8. A method in accordance with claim 1 wherein determining a change in the X-position, the Y-position, and the Z-position further comprises determining the change in the position an X-direction, a Y-direction, and a Z-direction, wherein the Y-direction is perpendicular to the X-direction and the Z-direction, and the X-direction is perpendicular to the Z-direction.

9. A method in accordance with claim 1 wherein determining a change in the X-position, the Y-position, and the Z-position further comprises outputting a plurality of determined positions at a frequency ranging from and including 100 hertz to ten kilohertz.

10. A method in accordance with claim 1 further comprising:
storing the at least one position within a storage device; and
diagnosing the X-ray image by applying the at least one position.

11. A method in accordance with claim 1 wherein determining a change in the X-position, the Y-position, and the Z-position of the first support further comprises determining the change in the X-position, the Y-position, and the Z-position of the first support according to the equation Position1=(a wavelength of the beam of light*the counted number of fringes between an initial position and Position1)*($\frac{1}{2}$), wherein Position1 is a position after the initial position.

12. A method in accordance with claim 1 further comprising outputting the determined change in the X-position, the Y-position, and the Z-position at each view angle of a predetermined series of view angles of the imaging system.

13. A system for generating an X-ray image of an object, said system comprising:
an X-ray imaging system comprising:
a first support for supporting the object;
a control mechanism configured to acquire X-ray image data of the object at a view angle with said first support at each position of a plurality of positions, each of said positions including an X-position, a Y-position, and a Z-position; and
an image reconstructor configured to reconstruct the X-ray image of the object using the acquired X-ray image data and a change in the X-position, a change in the Y-position, and a change in the Z-position of said first support at each of the plurality of positions; and
a position determination system comprising:
a light source configured to generate a beam of light;
a first reflective surface coupled to one of said first support and said object in a location to reflect at least a first portion of said beam of light to generate a reflected beam of light;
a beam splitter configured to combine the reflected beam with a second portion of the beam of light to generate a combined beam, said combined beam of light comprising an interference fringe pattern;
a photodetector configured to detect a number of fringes within said interference fringe pattern and to output a pulsed electric signal representative of a counted number of fringes; and
a processor configured to compute the change in the X-position, the change in the Y-position, and the change in the Z-position of the first support using said pulsed electric signal representative of said counted number of fringes.

14. A system in accordance with claim 13 further comprising:
a laser source configured to generate a first laser beam, wherein said beam splitter is further configured to split the first laser beam into a second laser beam and a third laser beam, wherein said first reflective surface is configured to generate a fourth laser beam from the second laser beam.

15. A system in accordance with claim 14 further comprising:
a second reflective surface coupled to a second support and configured to generate a fifth laser beam from the third laser beam.

16. A system in accordance with claim 14 further comprising:
a second reflective surface coupled to a second support and configured to generate a fifth laser beam from the third laser beam, wherein said beam splitter is further configured to generate said combined beam having said interference fringe pattern by combining the fourth and the fifth laser beams.

17. A system in accordance with claim 13 wherein said first reflective surface is coupled to a top of said first support, and said light source is coupled to a ceiling above said top of said first support, said beam of light directed downward from said light source toward said first reflective surface for determining a vertical position of said first support.

18. A system for generating an image of a subject, said system comprising:
an imaging system comprising:
an X-ray source configured to generate X-rays that pass through the subject;
an X-ray detector configured to detect the X-rays after the X-rays pass through the subject;
a first support configured to support the subject;
a control mechanism configured to acquire X-ray image data of the subject at a view angle with said first support at each of a plurality of positions, each of said positions including an X-position, a Y-position, and a Z-position; and
an image reconstructor configured to reconstruct the image of the subject using the acquired X-ray image data and a change in the X-position, a change in the Y-position, and a change in the Z-position of said first support at each of the plurality of positions; and
a position determination system comprising:
a light source configured to generate a beam of light;
a first reflective surface coupled to said first support in a location to reflect at least a portion of said beam of light from said first support to generate a reflected beam of light, said reflected beam of light comprising an interference fringe pattern;
a photodetector configured to detect a number of fringes within said interference fringe pattern and to output a pulsed electric signal representative of a counted number of fringes; and
a processor configured to compute the change in the X-position, the change in the Y-position, and the change in the Z-position of the first support using said pulsed electric signal representative of said counted number of fringes.

19. A system in accordance with claim 18 further comprising:
- a laser source configured to generate a first laser beam; and
- a beam splitter configured to split the first laser beam into a second laser beam and a third laser beam, wherein said first reflective surface is configured to generate a fourth laser beam from the second laser beam.

20. A system in accordance with claim 18 further comprising:
- a storage device configured to store the position, wherein said image reconstructor is configured reconstruct the image by applying the position.

* * * * *